US012697136B2

(12) United States Patent　　　　(10) Patent No.:　US 12,697,136 B2
Juergens et al.　　　　　　　　　　　(45) Date of Patent:　　　Aug. 4, 2026

(54) TROCAR FOR A SURGICAL INSTRUMENT

(71) Applicant: OLYMPUS Winter & Ibe GmbH, Hamburg (DE)

(72) Inventors: Thorsten Juergens, Hamburg (DE); Andreas Noe, Hamburg (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 133 days.

(21) Appl. No.: 18/645,919

(22) Filed: Apr. 25, 2024

(65) Prior Publication Data

US 2024/0366263 A1　　Nov. 7, 2024

Related U.S. Application Data

(60) Provisional application No. 63/464,266, filed on May 5, 2023.

(51) Int. Cl.
*A61B 17/34*　　　(2006.01)
*A61B 17/00*　　　(2006.01)
*A61B 34/30*　　　(2016.01)

(52) U.S. Cl.
CPC .... *A61B 17/3423* (2013.01); *A61B 17/00234* (2013.01); *A61B 34/30* (2016.02); *A61B 2017/00991* (2013.01)

(58) Field of Classification Search
CPC .......... A61B 17/00234; A61B 17/3421; A61B 17/3423; A61B 2017/00991; A61B 34/30
See application file for complete search history.

(56) References Cited

U.S. PATENT DOCUMENTS

| | | | | |
|---|---|---|---|---|
| 5,406,940 | A * | 4/1995 | Melzer ............... | A61B 17/3496 600/106 |
| 5,645,076 | A * | 7/1997 | Yoon .................. | A61B 17/3417 604/165.01 |
| 6,056,766 | A * | 5/2000 | Thompson ......... | A61B 17/3421 606/108 |
| 2008/0086165 | A1* | 4/2008 | Lyon ................. | A61M 25/0017 606/191 |
| 2012/0053577 | A1* | 3/2012 | Lee .................... | A61B 18/1815 606/33 |
| 2016/0361122 | A1* | 12/2016 | Seeber .................. | A61B 34/32 |
| 2017/0021127 | A1* | 1/2017 | Manouchehr ....... | A61M 5/3291 |
| 2017/0258489 | A1* | 9/2017 | Galili ..................... | A61B 10/04 |
| 2017/0333147 | A1* | 11/2017 | Bernstein ............... | A61B 46/10 |
| 2019/0059940 | A1* | 2/2019 | Cohen ................ | A61B 17/3494 |

(Continued)

FOREIGN PATENT DOCUMENTS

| | | | | |
|---|---|---|---|---|
| DE | 102009060377 | A1 * | 6/2011 | ......... A61B 17/3421 |
| DE | 102023111944 | A1 * | 11/2024 | ....... A61B 17/00234 |
| WO | WO-2013075205 | A1 * | 5/2013 | ............. A61B 34/30 |

*Primary Examiner* — Jacqueline T Johanas
(74) *Attorney, Agent, or Firm* — Scully, Scott, Murphy & Presser, P.C.

(57) ABSTRACT

A trocar for use with a surgical instrument. The trocar including; a proximal trocar head; a trocar shaft arranged on the trocar head, the trocar shaft is configured to receive an elongated shaft of the surgical instrument, and a positioning device provided on the proximal trocar head and being movable between retracted and extracted states relative to the trocar head, the positioning device being configured to position a distal end of the elongated shaft of the surgical instrument outside the trocar head in the extracted position.

17 Claims, 2 Drawing Sheets

(56)                    References Cited

U.S. PATENT DOCUMENTS

2019/0374249  A1*  12/2019  Abt ..................... A61B 17/3462
2020/0315721  A1*  10/2020  Rabindran ............. A61B 34/37
2021/0353328  A1*  11/2021  Cohen .................... A61B 90/50
2024/0366263  A1*  11/2024  Juergens ............ A61B 17/3423
2025/0017620  A1*   1/2025  Cohen ................ A61B 17/3496

* cited by examiner

TROCAR FOR A SURGICAL INSTRUMENT

CROSS-REFERENCE TO RELATED APPLICATION

The present application is based upon and claims the benefit of priority from U.S. Provisional Application No. 63/464,266, filed on May 5, 2023, the entire contents of which is incorporated herein by reference.

BACKGROUND

Field

The present disclosure relates to a trocar for a surgical instrument and to a surgical robot system with a surgical instrument, such as a laparoscope.

Prior Art

In the prior art, endoscopes, such as video endoscopes, are known which are utilized, for example, to treat humans. Video endoscopes have an elongated, tubular endoscope shaft, on the distal end of which a distally radiating illumination device and an image sensor or respectively an image sensor unit for capturing images from the surroundings of the distal end are provided.

Moreover, it is known that trocar sleeves are used for minimally invasive surgery in order to provide access to a body cavity or body space. Here, trocars having a hollow shaft are used, for example, in laparoscopy, by which access to an abdominal cavity of a body of a living being is formed. During the minimally invasive procedure, for example, an endoscope or respectively laparoscope or a surgical tool is inserted through the hollow shafts of the trocar sleeves.

SUMMARY

An object is to provide a trocar for the surgery procedures, such as for robotic assisted surgeries.

Such object can be solved by a trocar for a surgical instrument with a proximal trocar head and a trocar shaft arranged on the trocar head for receiving an elongated shaft of a surgical instrument, such as a laparoscope, wherein a positioning device for positioning a distal end of the elongated shaft of the surgical instrument outside the trocar head is provided on the proximal trocar head on a side facing away from the trocar shaft.

A surgical instrument, such as the distal end of the surgical instrument, can be positioned outside the insert opening of the trocar head by the positioning device. The positioning device can be configured to hold the distal end of the surgical instrument for inspection and/or for cleaning the distal end before inserting the distal end and the shaft of the surgical instrument into the insert opening of the trocar head. The trocar can be used for robotic assisted surgery, wherein the distal end of the surgical instrument can be positioned and/or held before inserting the shaft of the surgical instrument into the trocar head and/or after retracting the shaft out of the trocar head. Furthermore, the distal end of the surgical instrument can be fixed and/or locked outside the trocar head by the external positioning device.

The surgical instrument can be configured as a laparoscope or endoscope or the like, wherein the surgical instrument can be equipped or have a shaft with a distal end. The distal end of the shaft can have a window for detection, such as optical detection, of the inspected area around the distal end.

After retraction of the surgical instrument out of the trocar head and positioning of the distal end of the surgical instrument at a predetermined distance from the insertion opening of the trocar head, an additional docking procedure can be omitted, such as for the robotic assisted surgery, for the insertion or the re-insertion of the shaft of the surgical instrument into the trocar head. Hereby, the application of the robotic assisted surgery or of a surgical robot system can be enhanced and improved. For surgical robot systems the reference position of the shaft of the surgical instrument or the reference position of the distal end of the surgical instrument can be registered at the beginning of the surgery or the operation by the positioning device so that the surgical instrument can be several times inserted into or retracted out of the trocar head without the registration of further reference positions (of the shaft or the distal end of the endoscope).

According to an embodiment of the trocar, the positioning device can be arranged such that when the distal end of the elongated shaft of the surgical instrument is positioned outside the trocar head, a window, such as a distal window, of the distal end of the elongated shaft of the surgical instrument can be accessible.

In a further embodiment, the positioning device can comprise an insertion opening for the elongated shaft of the surgical instrument facing away from the proximal trocar head.

The insertion opening of the positioning device can be formed as a sleeve-like section or a sleeve.

A further embodiment of the trocar can further comprise a retaining device for retaining the sleeve-like section or the sleeve on the trocar head.

Besides, in a further embodiment the positioning device can be configured as a telescopic tube section, such as with an insertion opening for the elongated shaft of the surgical instrument.

With relation to the longitudinal extension of the trocar shaft, the telescopic tube section can be configured to be movable relative to the trocar shaft.

At least one end stop or two end stops can be provided for the telescopic tube section.

According to an embodiment, when the telescopic tube section is positioned at an end stop, the telescopic tube section can be locked or can be locked by a locking device.

The telescopic tube section in a retracted state can be at least partially received in the interior of the trocar shaft.

Moreover, such object can be solved by a surgical robot system with a surgical instrument, such as a laparoscope, a robot for operating the surgical instrument and with a trocar of the surgical instrument as described above. In order to avoid unnecessary repetitions, reference is expressly made to the above explanations.

BRIEF DESCRIPTION OF THE DRAWINGS

Further features will become evident from the description of embodiments, together with the claims and the appended drawings. Embodiments can fulfill individual features or a combination of several features.

The embodiments described below, without restricting the general intent of the invention, based on exemplary embodiments, wherein reference is made expressly to the drawings with regard to the disclosure of all details that are not explained in greater detail in the text.

In the drawings:

FIG. 1a illustrates a schematic perspective view of a trocar with a positioning device in retracted state;

FIG. 1b illustrates a schematic perspective view of a trocar with a positioning device in extracted state;

FIG. 2a illustrates a schematic perspective view of a positioning device according to another embodiment;

FIG. 2b illustrates a schematic perspective view of a positioning device according to a further embodiment; and FIG. 3 illustrates a schematic perspective view of a trocar with a positioning device and a distal end of a laparoscope positioned in the positioning device of the trocar.

In the drawings, the same or similar types of elements or respectively corresponding parts are provided with the same reference numbers in order to prevent the item from needing to be reintroduced.

DETAILED DESCRIPTION

Figures 1A, 1B:
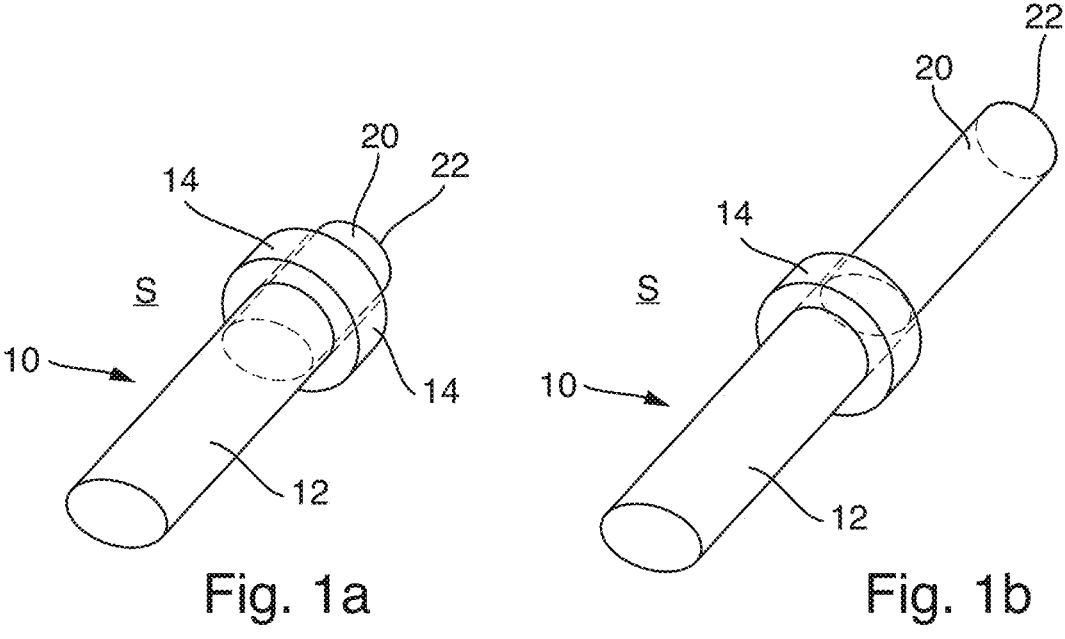

In FIG. 1a is a schematic perspective view of a trocar 10 with a positioning device 20 in a retracted state, while FIG. 1b shows a schematic perspective view of a trocar with the positioning device 20 in an extracted state. The trocar 10 is part of a surgical system, such as a surgical robot system designated with S (shown schematically by dashed line S in FIG. 3).

The trocar 10 comprises a trocar shaft 12 for accommodating the shaft of a surgical instrument such as a laparoscope. At the proximal end of the trocar shaft 12 the trocar 10 comprises a trocar head 14. The positioning device 20 is arranged movable in the trocar shaft 12 at the proximal end of the trocar shaft 12. The positioning device can be linearly movable between the retracted state (see FIG. 1a) and the extracted state (see FIG. 1b). In the retracted state, the distal end of the positioning device 20 and/or a distal end of a surgical instrument inserted therein can extend distally from the distal end of the trocar shaft.

In the extracted state of the positioning device 20, a distal end of the surgical instrument can be positioned outside the trocar head 14, wherein the distal end of the surgical instrument is held or positioned by the positioning device. The distal end of the surgical instrument can be positioned between a proximal end 22 and a distal end 24 of the positioning device 20. The proximal end 22 and the distal end 24 of the positioning device are each provided with an opening for the insertion and accommodating of the distal end of the shaft of the surgical instrument or the shaft of the surgical instrument.

The positioning device 20 in FIGS. 1a and 1n FIG. 1b is configured as a sleeve-like tube or as a sleeve tube and the like having distal and proximal openings for insertion of the surgical instrument therethrough. An outer surface of the sleeve tube can have sliding or close contact with an inner surface of the trocar shaft. Moreover, the positioning device 20 can be provided with recesses between the proximal end 22 and the distal end 24 in order to provide access to a window of the distal end of a surgical instrument, when the distal end of the surgical instrument is positioned outside the trocar shaft 12 and/or the trocar head 14.

The positioning device 20 can be configured as a telescopic tube which can be inserted into the trocar shaft 12 or can be extracted or extended from the trocar shaft 12. The positioning device is referred to as a telescopic tube in that it is at least telescopic with regard to the trocar shaft 12. In normal operation, the positioning device 20 is positioned inside the trocar 10, such as inside the trocar shaft 12. The telescopic function of the positioning device is to avoid that a surgical instrument after retraction out of the trocar 10 loses the active working length of the surgical system.

The positioning device 20 makes it possible that a surgical instrument is still tightly coupled with the trocar 10 after retraction of the surgical instrument out of the trocar 10. Hereby, the surgical instrument can be easily cleaned outside the trocar 10 without undocking the extracted surgical instrument with the trocar 10. Further embodiments of the positioning device 20 are shown in the schematic perspective views of FIG. 2a and FIG. 2b. The embodiment of the positioning device 20 in FIG. 2a comprises at the proximal end 22 and at the distal end 24 each a sleeve tube section, which are connected by at least one connecting bar 26. The connecting bar (also referred to as a retaining device) retains the distal end 24 relative to the proximal end 22. According to further embodiments, the proximal end 22 and the distal end 24 of the positioning device 20 are connected by several connecting bars.

Furthermore, the sleeve-like proximal end 22 and the sleeve-like distal end 24 are each provided with a projection 28, 29 as stops, which are projecting outwardly in the radial direction of the proximal end 22 and the distal end 24. The projections 28, 29 cooperate with undercuts or the like of the trocar shaft 12 in order to limit the movement of the positioning device 20. By the projections 28, 29 the positioning device 20 can be locked in the retracted state and/or in the extracted state of the positioning device.

Figures 2A, 2B:
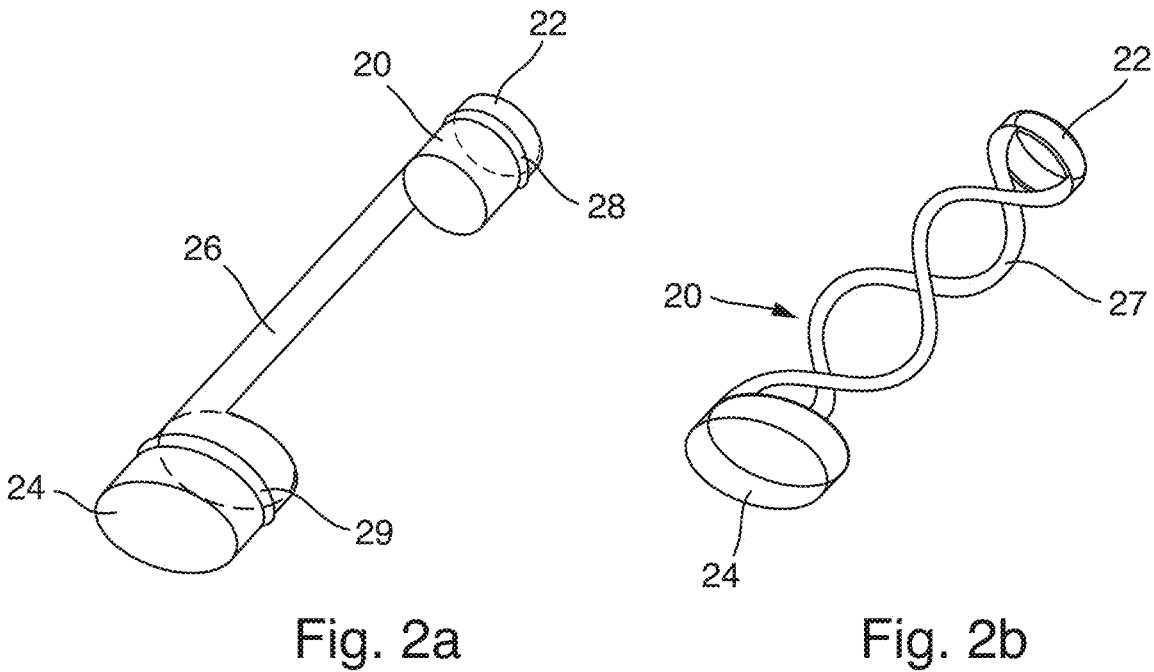

According to the further shown embodiment of the positioning device 20 in FIG. 2b, the proximal end 22 and the distal end 24 of the positioning device 20 are connected by more than one connecting bar each having a helical structure, a fillet or a framework structure 27 or the like. The framework structure 27 provides several accesses to a window of the distal end of a surgical instrument, in case the distal end is arranged or positioned in the positioning device 20 between the proximal end 22 and the distal end 24.

Figure 3:
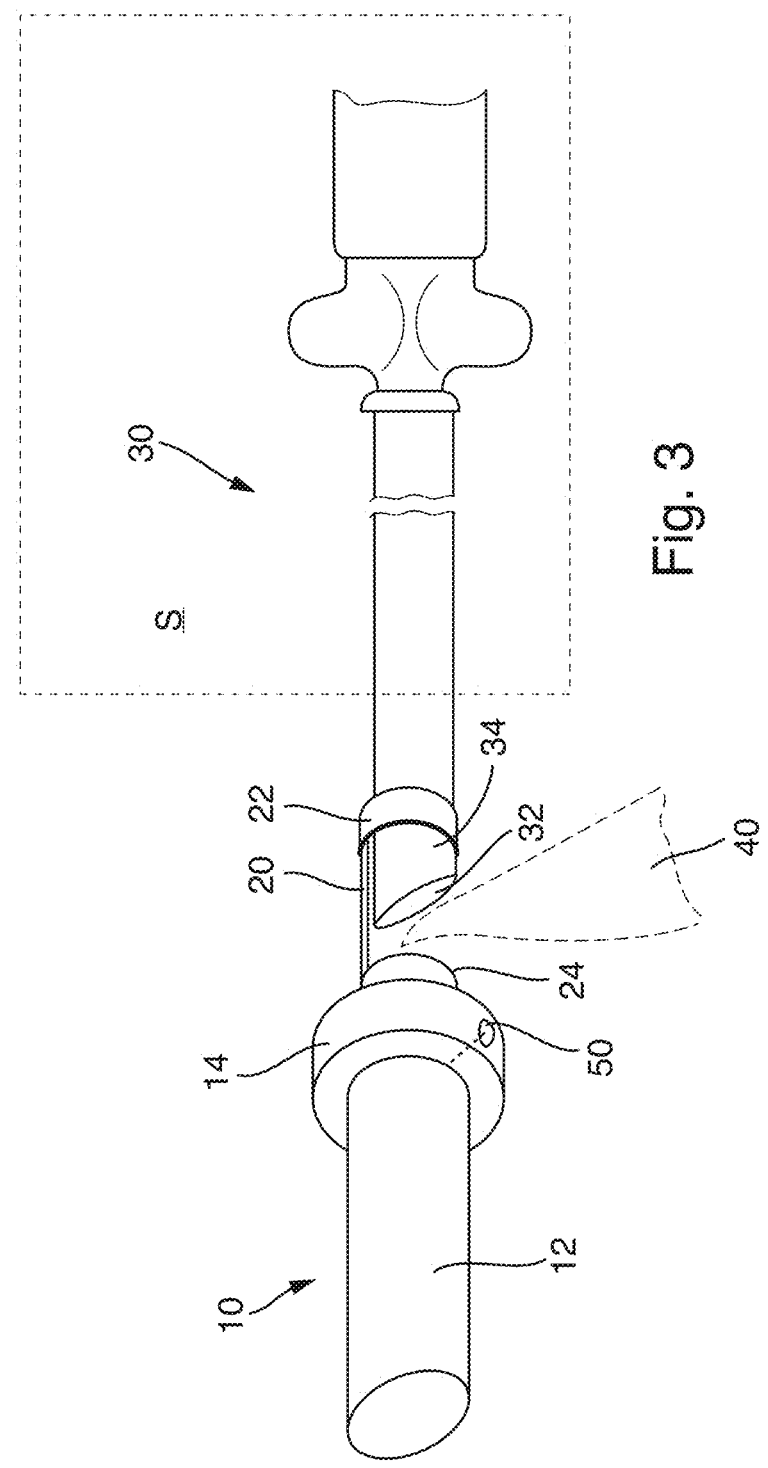

The illustration of FIG. 3 shows a schematic perspective view of a trocar 10 with a positioning device 20, wherein a distal end 34 of a laparoscope 30 is positioned in the extracted positioning device 20 of the trocar 10. The distal end 34 of the laparoscope 30 is provided with a window 32, which can be made out of glass. At the position of the distal end 34 of the laparoscope between the sleeve-like proximal end 22 and the sleeve-like distal end 24 of the positioning device, the window 32 is accessible for cleaning, for example using a cleaning swap or a cleaning tissue 40. Hereby, the docking between the trocar 10 and the laparoscope 30 is ensured.

The extraction or the retraction of the telescopic positioning device 20 can be controlled or locked during the operation of the trocar or the surgical system. The telescopic positioning device 20 can be locked in the retracted position in the trocar shaft 12 by a button 50 of a locking device. By pressing the button 50 the retracted positioning device 20 can be released and thus the positioning device 20 can be pushed into the extracted or extended position outside the trocar 10 or the trocar head 14. Furthermore, in a further embodiment, the extracted telescopic positioning device 20 can be locked and/or released by operation of the button 50 or another control member (the button 50 being part of a locking device operatively connected to the positioning device 20, indicated schematically by dashed line).

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS 10 trocar
12 trocar shaft
14 trocar head
20 positioning device
22 proximal end
24 distal end
26 connecting bar
27 framework structure
28 projection
29 projection
30 laparoscope
32 window
34 distal end
40 cleaning tissue
50 button
S surgical robot system

What is claimed is:

1. A trocar for use with a surgical instrument, the trocar comprising:
a proximal trocar head;
a trocar shaft arranged on the trocar head, the trocar shaft is configured to receive an elongated shaft of the surgical instrument; and
a positioning device provided on the proximal trocar head and being movable between retracted and extracted states relative to the trocar head, the positioning device being configured to position a distal end of the elongated shaft of the surgical instrument outside the trocar head in the extracted position;
wherein the positioning device is a telescopic tube section having an insertion opening for the elongated shaft of the surgical instrument; and
the telescopic tube section is at least partially received in an interior of the trocar shaft in the retracted state.

2. The trocar according to claim 1, wherein the telescopic tube section is arranged such that when the distal end of the elongated shaft of the surgical instrument is positioned outside the trocar head, a window of the distal end of the elongated shaft of the surgical instrument is accessible.

3. The trocar according to claim 1, wherein the positioning device is an elongated sleeve.

4. The trocar according to claim 3, further comprising a retaining device provided on the elongated sleeve for retaining the elongated sleeve on the trocar head.

5. The trocar according to claim 1, wherein the telescopic tube section is configured to be movable relative to the trocar shaft.

6. The trocar according to claim 1, wherein the telescopic tube section further comprising at least one end stop for limiting a movement of the telescopic tube section.

7. The trocar according to claim 6, further comprising a locking device at the at least one end stop for locking movement of the at least one telescopic tube section.

8. The trocar according to claim 1, wherein the telescopic tube section comprises a distal end and a proximal end and one or more connecting bars connecting the distal end and the proximal end.

9. The trocar according to claim 8, wherein the one or more connecting bars comprises a connecting bar extending linearly along a longitudinal direction of the telescopic tube section.

10. The trocar according to claim 8, wherein the one or more connecting bars comprises two or more connecting bars extending helically along a longitudinal direction of the telescopic tube section.

11. The trocar according to claim 8, wherein the telescopic tube section comprises an end stop for limiting a movement of the positioning device relative to a longitudinal direction of the trocar shaft, the end stop being provided on one or more of the distal end and the proximal end of the positioning device.

12. The trocar according to claim 1, wherein the trocar head has a greater size in a direction orthogonal to a longitudinal axis of the trocar shaft than a size of the trocar shaft in the direction orthogonal to the longitudinal axis of the trocar shaft.

13. A surgical robot system with a surgical instrument comprising:
a robot for operating the surgical instrument; and
the trocar according to claim 1 for holding the surgical instrument.

14. A surgical system comprising:
a surgical instrument having an elongated shaft; and
the trocar according to claim 1 for holding the surgical instrument.

15. A trocar for use with a surgical instrument, the trocar comprising:
a proximal trocar head;
a trocar shaft arranged on the trocar head, the trocar shaft is configured to receive an elongated shaft of the surgical instrument; and
a positioning device provided on the proximal trocar head and being movable between retracted and extracted states relative to the trocar head, the positioning device being configured to position a distal end of the elongated shaft of the surgical instrument outside the trocar head in the extracted position;
wherein the positioning device is a telescopic tube section having an insertion opening for the elongated shaft of the surgical instrument;
the telescopic tube section comprises a distal end and a proximal end and one or more connecting bars connecting the distal end and the proximal end; and
the one or more connecting bars comprises two or more connecting bars extending helically along a longitudinal direction of the telescopic tube section.

16. A surgical robot system with a surgical instrument comprising:
a robot for operating the surgical instrument; and
the trocar according to claim 15 for holding the surgical instrument.

17. A surgical system comprising:
a surgical instrument having an elongated shaft; and
the trocar according to claim 15 for holding the surgical instrument.

* * * * *